United States Patent [19]

Latucca et al.

[11] 4,336,797

[45] Jun. 29, 1982

[54] ADJUSTABLE SURGICAL DRAPE

[76] Inventors: Vincent Latucca, 245 E. 57 St., New York, N.Y. 10022; Burton Bronsther, 195 Village Ave., Rockville Center, N.Y. 11570

[21] Appl. No.: 180,591

[22] Filed: Aug. 25, 1980

[51] Int. Cl.³ .............................................. A61F 13/00
[52] U.S. Cl. .............................................. 128/132 D
[58] Field of Search ............... 128/132 R, 132 D, 292, 128/296

[56] References Cited

U.S. PATENT DOCUMENTS

| 4,027,665 | 6/1977 | Scrivens | 128/132 D |
| 4,134,398 | 1/1979 | Scrivens | 128/132 D |
| 4,196,723 | 4/1980 | Moose, Jr. | 128/132 D |

Primary Examiner—C. Fred Rosenbaum
Attorney, Agent, or Firm—Hubbell, Cohen, Stiefel & Gross

[57] ABSTRACT

Improved surgical drape (20) comprises a flexible, drapable main sheet (22) having a fenestration (30) therein, a closure member (38, 40), and means (34) for movably securing the closure member (38, 40) to the main sheet (22) for selectively obstructing at least part of the fenestration (30).

12 Claims, 12 Drawing Figures

ADJUSTABLE SURGICAL DRAPE

TECHNICAL FIELD

The present invention pertains to a utility surgical drape and more particulary to a surgical drape having a variable fenestration therein.

BACKGROUND ART

The need for a surgical drape provided with different sized fenestrations has been recognized in the art. Thus, U.S. Pat. No. 4,027,665 issued to Scrivens discloses a cardiovascular drape having at least two rectangular openings in order to allow the surgeon access to various operation sites without the need for mulitple drapes. Likewise, U.S. Pat. No. 4,024,862 issued to Collins discloses a surgical drape having multiple removable frame sheets, each with a different sized opening therein. Although fenestrations of various sizes are provided by the device of the latter patent, the size of the fenestrations in each frame sheet is fixed. The prior art drape disclosed in the Collins patent is further disadvantageous in that all surgical tools must be removed from the patient before a frame sheet can be added or removed for changing the size of the fenestration. This is burdensome and time consuming to the surgical team, and may even be hazardous to the patient.

DISCLOSURE OF THE INVENTION

A principal object of the present invention is to provide means for varying the size of the fenestration in a surgical drape which does not require changing the drape or removing parts therefrom.

The preferred drape of the present invention comprises a flexible drapable main sheet having an upper surface and a lower surface, the latter contacting the patient when the drape is applied. The drape is provided with at least one preferably substantially rectangular fenestration. A frame sheet having a fenestration therein is secured to the upper surface of the main sheet such that the fenestrations in the main sheet and frame sheet are aligned. Preferably two panels are slidably secured between the upper surface of the main sheet and the frame sheet for selectively obstructing at least part of the opening defined by the aligned fenestrations. Depending on the surgical procedure to be performed, any desired opening may be selected by simply adjusting the positions of the panels until the desired opening is exposed.

Other means may be utilized for slidably securing the panels to the main sheet. For example, in another embodiment of the present invention a main sheet having a fenestration therein is provided on its upper surface with tracks or grooves preferably made of flexible plastic material. The tracks extend along opposite sides of the fenestration. Preferably two sliding panels are provided with mating ridges extending parallel to and aligned with the tracks on the main sheet whereby the ridges may be snapped or otherwise movably secured to the tracks. It will thus be apparent that the size of the opening may be varied by sliding the panels along the tracks. Still other embodiments are possible, some of which will be described hereinafter.

Further features and advantages of the invention will become more fully apparent from the following detailed description and annexed drawings of the presently preferred embodiments thereof.

BEST MODE FOR CARRYING OUT THE INVENTION

Figure 1:
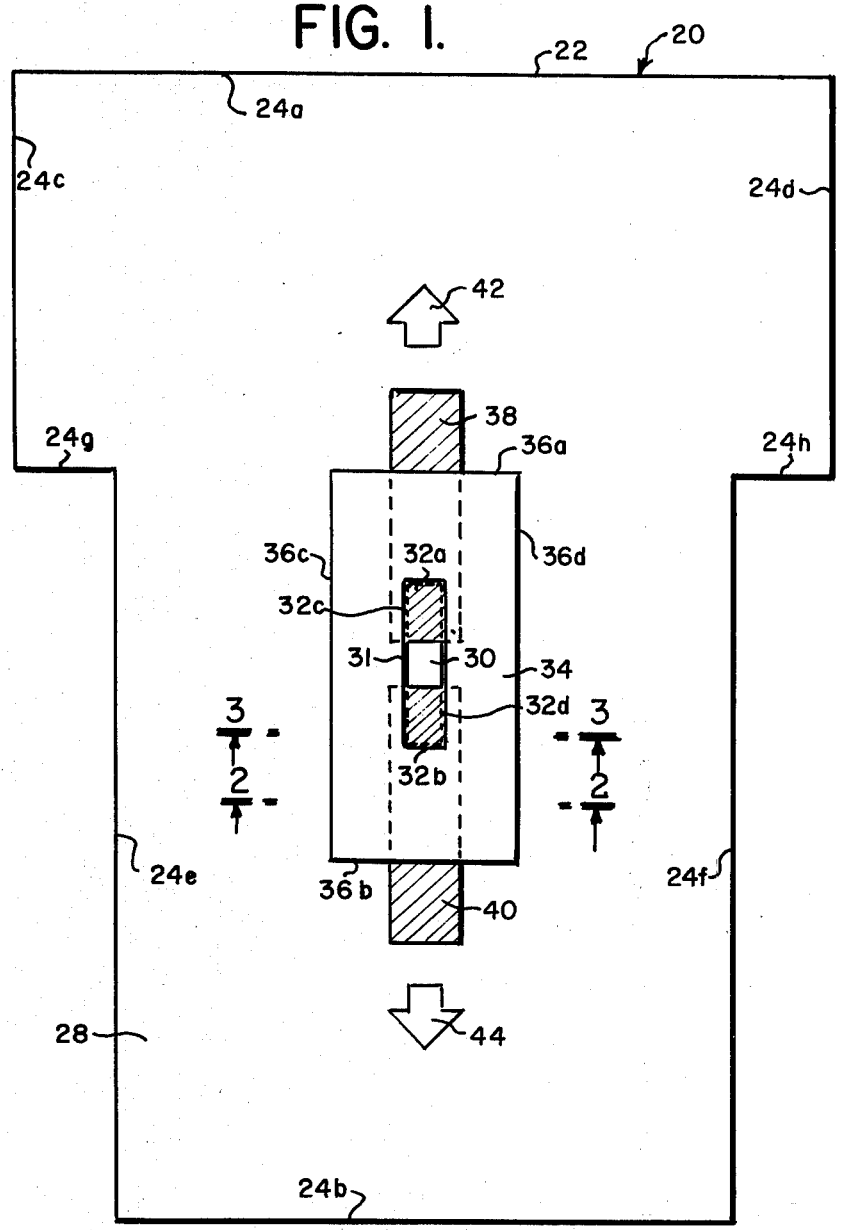
FIG. 1 is a top plan view of the surgical drape of the present invention.
Figure 2:
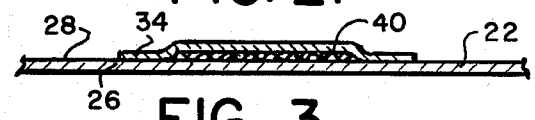
FIG. 2 is fragmentary crossectional view taken along the line 2—2 in FIG. 1.
Figure 3:
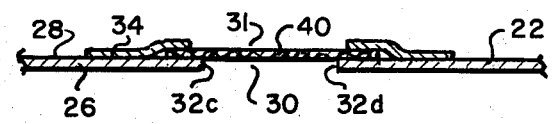
FIG. 3 is a fragmentary cross-sectional view taken along the line 3—3 in FIG. 1.

Referring initially to FIGS. 1-3, there is shown a surgical drape 20 as used, e.g., for laparotomy procedures on children and adults. The drape 20 may be comprised of any suitable flexible material such as cotton, non-woven fabric, plastic or the like. Most preferably, the drape 20 is comprised of a wet laid, non-woven or multilayer cellulose based, scrim reinforced, material. The material is preferably fluid repellent and exhibits low lint. The drape 20 includes a preferably T-shaped main sheet 22, although the sheet 22 can also be of any other size or shape sufficient to substantially cover the body of a patient. As shown, the main sheet 22 has a top edge 24a, a parallel bottom edge 24b, two parallel lateral edges 24c and 24d, two parallel lateral edges 24e and 24f and two edges 24g and 24h connecting, respectively, edge 24c with edge 24e and edge 24d with edge 24f. The sheet 22 has a preferably rectangular fenestration 30 defined by the edges 32a, 32b, 32c and 32d. The lower surface 26 of the sheet 22 faces the patient when the drape is applied.

Drape 20 also includes a perferably rectangular frame sheet 34 having a top edge 36a, a bottom edge 36b and side edges 36c and 36d. The frame sheet 34 has a fenestration 31 which is preferably slightly larger than the fenestration 30 in the main sheet 22. The frame sheet 34 may comprise the same material as main sheet 22. Preferably, the upper surface of the frame sheet is provided with a multilayer polyethylene foam lamination to prevent sliding of surgical tools placed thereon. The edges 36c and 36d of the frame sheet 34 are affixed, as a gluing, heat sealing or sewing, to the upper surface 28 of the main sheet 22, such that the fenestrations 30 and 31 are substantially aligned. Two preferably rectangular panels 38 and 40 are slidably inserted between the main sheet 22 and the frame sheet 34 through the slits defined by the unsecured edges 36a, 36b of the frame sheet. By pulling one or both of the sliding panels 38 and 40 in the direction of arrows 42 and 44, respectively, any desired portion of the opening defined by the aligned fenestrations 30, 31 may be exposed. In a preferred embodiment, the edges 24c, 24d of the main sheet 22 are 44 inches, the edges 24e and 24f are 88 inches, the top edge 24a is 100 inches, and the bottom edge 24b is 77 inches. The length of the edges 36c and 36d of the frame sheet 34 is 44 inches and the length of the edges 36a and 36b of frame sheet 34 is 22 inches. The above dimensions are found to be particularly preferable if the surgical drape 20 is used for a laparotomy procedure. Preferably, fenestration 31 of frame sheet 34 is 18 inches long and 4 inches wide and the sliding panels 38, 40 are 28 inches long and 8 inches wide. In any case, the sliding panels 38, 40 must be sufficiently long such that in all positions thereof a portion of their free ends extend beyone the edges 36a and 36b, respectively, whereby the free ends are accessible for slidably adjusting the positions of the panels. Of course, the dimensions of the surgical drape may vary according to the type of surgical procedure to be performed and the size of the patient.

Figure 4:
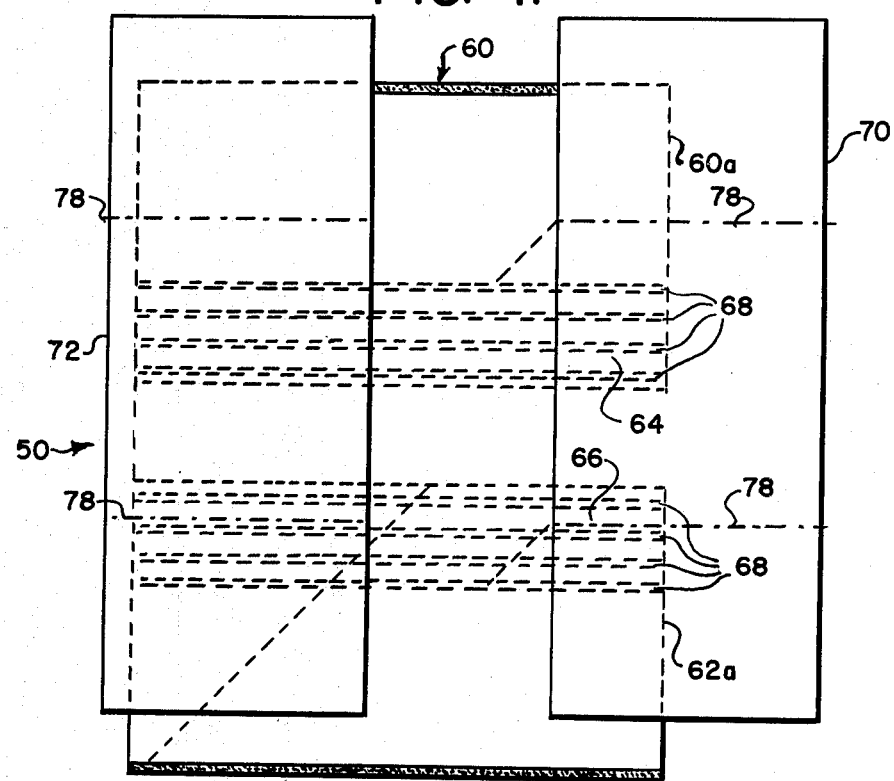
FIG. 4 is an exploded view of another embodiment of the drape of the present invention.

Another embodiment 50 of the present invention is illustrated in FIGS. 4-7. Referring first to FIG. 4, the drape 50 includes two spaced apart, coplanar, preferably rectangular bottom sheets 60, 62. As shown, the confronting edges of the sheets 60, 62 are sufficiently spaced to allow access to the operation site. Bottom sheets 60 and 62 are provided on their upper surfaces 64 and 66, respectively, with a plurality of grooves or tracks 68, shown by way of example as four tracks 68. The tracks 68 are affixed to the upper surfaces of the bottom sheets by any suitable method, such as sewing, gluing, or heat sealing. As shown, tracks 68 are parallel and extend along the entire length of the sheets 60, 62 adjacent the confronting edges thereof. Two top sheets 70 and 72, also having preferably rectangular shapes, perpendicularly overly the bottom sheets 60 and 62. The lower surface of each top sheet 70, 72 is provided with a pair of parallel ridges 78, each ridge being dimensioned for a sliding fit in one of the tracks 68.

Figure 5:
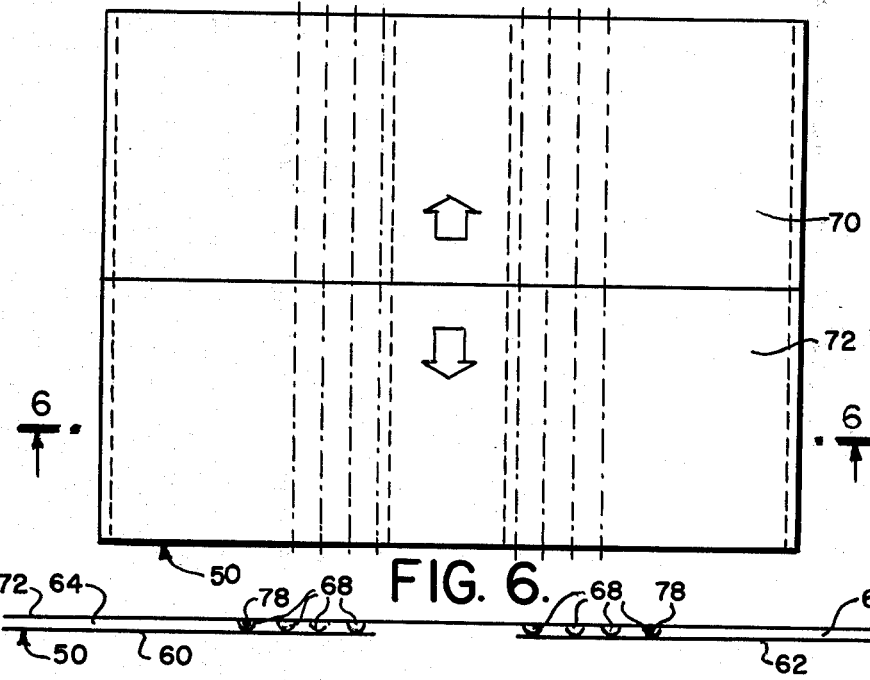
FIG. 5 is a top plan view of the drape of FIG. 4, showing the drape in the fully closed position.
Figure 6:
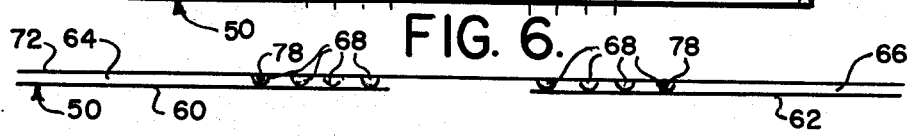
FIG. 6 is a cross-sectional view taken along the line 6—6 in FIG. 5.
Figure 6A:
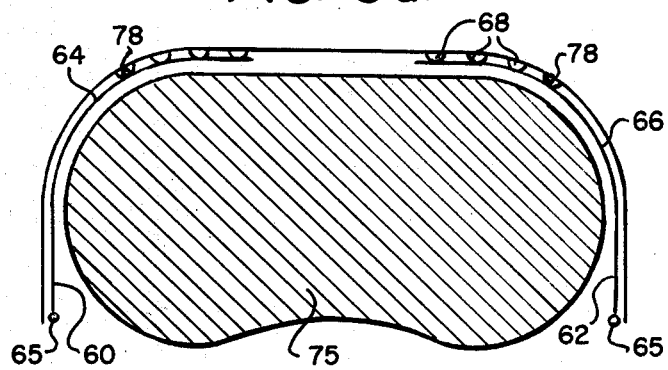
FIG. 6a is a cross-sectional view showing the drape of FIGS. 4 and 5 applied to a patient.
Figure 7:
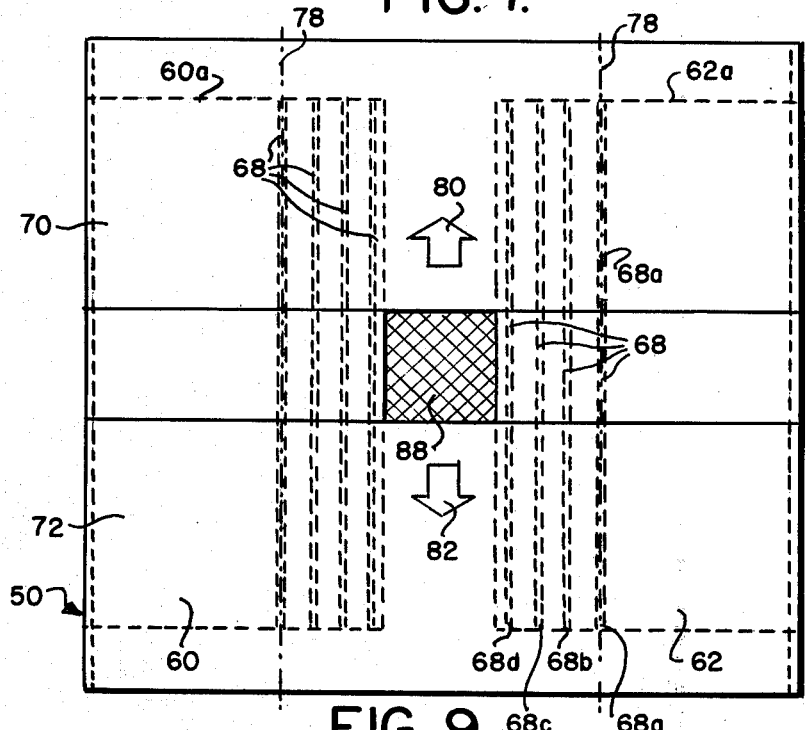
FIG. 7 is a top plan view of the drape of FIGS. 4-6 showing the drape in a partially open position.
Figure 9:
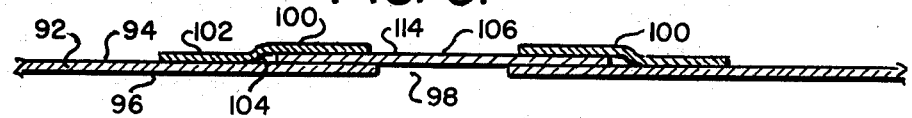
FIG. 9 is a fragmentary cross-sectional view taken along the line 9—9 in FIG. 8.
Figure 10:
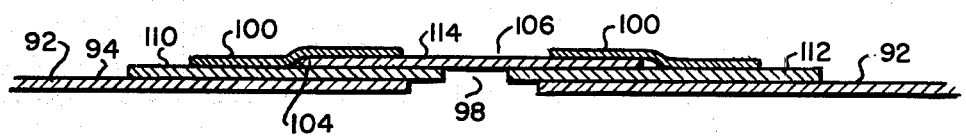
FIG. 10 is a fragmentary cross-sectional view taken along the line 10—10 in FIG. 8.

Referring now to FIGS. 5-7, during use of the drape 50, the four sheets 60, 62, 70 and 72 are placed over the patient such that the edges 60a and 62a of the bottom sheets 60 and 62, respectively, are pointing toward the head of the patient. One of the ridges 78 of each top sheet 70, 72 is slidably seated in one track 68a in the bottom sheet 60, and 62, respectively. Referring to FIG. 7, it will thus be apparent that any desired width for the fenestration 88 defined between the bottom sheets 60, 62 may be selected by simply sliding one or both of the top sheets 70, 72 in the direction indicated by arrows 80, 82. In FIG. 5, the top sheets 70, 72 are shown in their fully closed positions wherein the fenestration 88 is wholly obstructed. The spacing between the bottom sheets 60 and 62 can also be adjusted by removing the ridges 78 from the tracks 68a and inserting them into tracks 68b, 68c or 68d. It will thus be apparant that any length or width for the fenestration 88 may be selected. As best shown in FIG. 6a, bottom sheets 60 and 62 may be provided with a weighted seam 65 to hold the drape 50 securely in place on the patient 75. The drape 50 is preferably composed of the same material suggested for the drape 20 of FIGS. 1-3.

Figure 8:
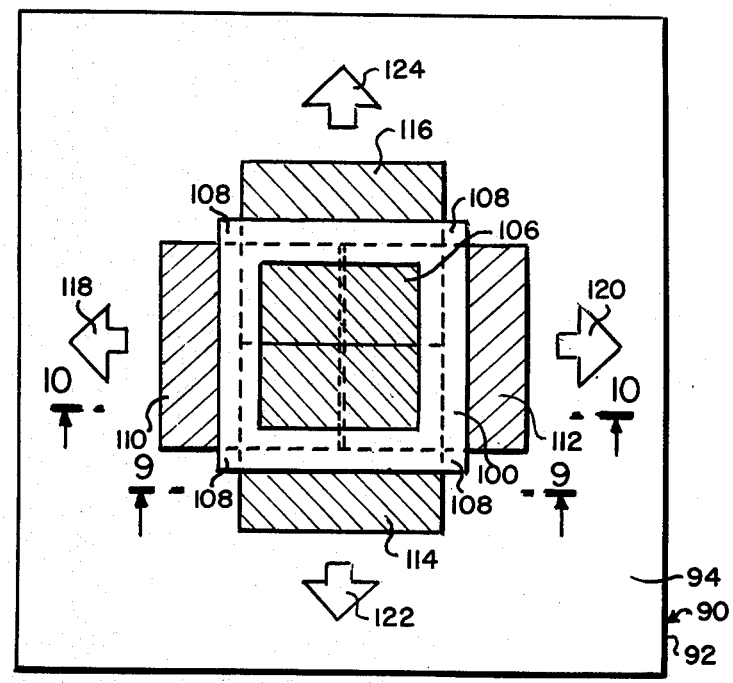
FIG. 8 is a top plan view of another embodiment of the present invention.
Figure 11:
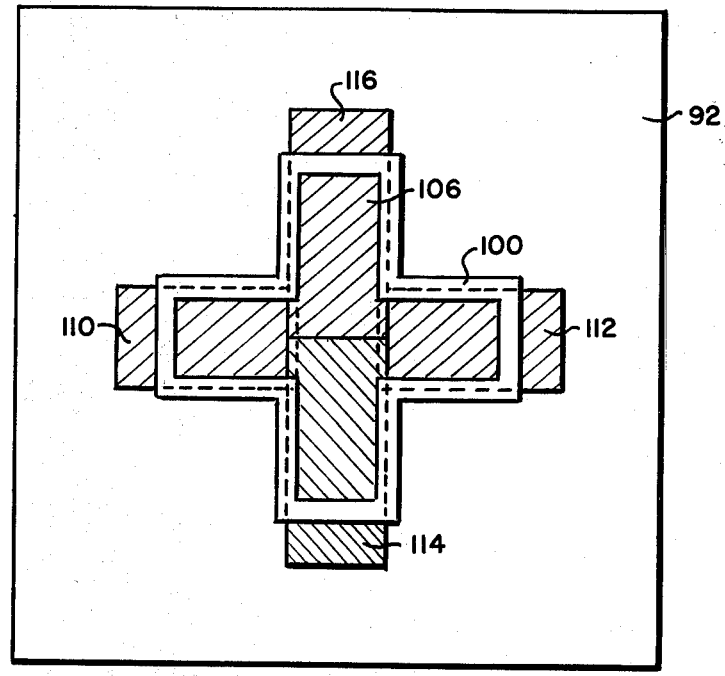
FIG. 11 is a top plan view of still another embodiment of the drape of the present invention.

Still another embodiment 90 of the invention is shown in FIGS. 8-11. The surgical drape 90 comprises a main sheet 92 having upper and lower surfaces 94 and 96 and a fenestration 98. Overlying fenestration 98 is a frame sheet 100 having upper and lower surfaces 102 and 104, respectively. The frame sheet 100 has a fenestration 106 therein which is preferably slightly larger than the fenestration 98 in the main sheet 92. The corners 108 of the frame sheet 100 are secured to the upper surface 94 of the main sheet 92 (FIG. 8). This may be accomplished by any suitable method such as those suggested above in connection with FIGS. 1-3 for securing frame sheet 34 to main sheet 22.

Four panels 110, 112, 114 and 116 are slidably inserted between the frame sheet 100 and main sheet 92 through the four slits defined between the secured corners 108 of the frame sheet 100. The pair of panels 114, 116 preferably overly the panels 110, 112. By suitably adjusting the positions of the panels, any size rectangular opening may be obtained. Thus, in FIG. 8 the panels 110, 112, 114, 116 fully obstruct the opening defined by the aligned fenestrations 98, 106. The opening may be exposed to any desired extent by pulling the panels 110, 112, 114, 116 in the directions indicated by the arrows 118, 120, 122 and 124, respectively. The fenestrations 98, 106 may take any desired shape, such as rectangular as in FIG. 8, circular, or even cross, as in FIG. 11.

By way of example, the main sheet 92 may be 60 inches×60 inches, the fenestration 106 18 inches×18 inches, the sliding panels 110, 112, 114 and 116 each 20 inches×20 inches and the frame sheet 100 about 30 inches×30 inches. Preferably, the drape 90 is comprised of the same material suggested for the drape 20 of FIGS. 1-3.

Since these as well as further embodiments and modifications thereto are intended to be within the scope of the present invention, the above description should be construed as illustrative and not in a limiting sense, the scope of the invention being defined by the following claims.

We claim:

1. A surgical drape comprising:
   a flexible drapable main sheet having upper and lower surfaces, said main sheet having a fenestration therein; a closure member having upper and lower surfaces disposed in overlapping relation with said main sheet; and means for securing said closure member to said main sheet for sliding movement relative thereto for selectively obstructing any desired portion of said fenestration.

2. The drape according to claim 1, wherein said securing means comprises:
   a frame sheet having a fenestration therein, said frame sheet being secured along a portion of its periphery to said upper surface of said main sheet with the fenestration in said frame sheet aligned with said fenestration in said main sheet, said closure member being slidably movable between said main sheet and said frame sheet through the opening defined by the unsecured peripheral portion of said frame sheet for selectively obstructing said fenestration in said main sheet.

3. The drape according to claim 2, wherein said frame sheet comprises a substantially rectangular member, said secured portion of said periphery of said frame sheet comprises a pair of opposite edges thereof, and wherein said closure member comprises two substantially rectangular panels slidably inserted between the pair of openings defined by the pair of unsecured edges of said frame sheet.

4. The drape according to claim 2, wherein said frame sheet comprises a substantially rectangular member, the secured peripheral portion of said frame sheet comprises the corners of said frame sheet, and wherein said closure member comprises four substantially rectangular panels, one inserted through each of the four openings defined between the secured corners of said frame sheet, the panels inserted between one pair of opposite openings in said frame sheet overlying the panels inserted between the other pair of opposite openings in said frame sheet.

5. The drape according to claim 3 or 4, wherein said fenestrations are rectangular.

6. The drape according to claim 4, wherein said fenestrations are cross-shaped.

7. The drape according to claim 1, wherein said securing means comprises a pair of tracks affixed to said upper surface of said main sheet, and a pair of mating ridges affixed to said lower surface of said closure member, said ridges being inserted in said tracks for sliding movement therein.

8. The drape according to claim 7, wherein said pair of tracks are secured to said upper surface of said main sheet on opposite sides of said fenestration, and wherein said closure member comprises two panels, each having a pair of mating ridges on the lower surfaces thereof.

9. The drape according to claim 8, wherein said main sheet comprises two coplanar bottom sheets in confronting relation along respective edges thereof, said fenestration comprising the space between said confronting bottom sheets.

10. The drape according to claim 9, and further comprising one or more additional tracks on each side of said fenestration whereby the apacing between said bottom sheets may be adjusted.

11. The drape according to claim 10, wherein said panels are substantially rectangular, and wherein said tracks are substantially parallel and extend adjacent the confronting edges of said bottom sheets.

12. The drape according to claim 11, wherein said edges of said bottom sheet opposite said confronting edges are weighted.

* * * * *